(12) United States Patent
Moretti et al.

(10) Patent No.: US 7,592,492 B2
(45) Date of Patent: Sep. 22, 2009

(54) PATCHOULI ODORANT

(75) Inventors: Robert Moretti, Grand-Lancy (CH); Olivier Etter, Chene-Bourg (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 12/300,570

(22) PCT Filed: May 3, 2007

(86) PCT No.: PCT/IB2007/051654

§ 371 (c)(1),
(2), (4) Date: Nov. 12, 2008

(87) PCT Pub. No.: WO2007/135582

PCT Pub. Date: Nov. 29, 2007

(65) Prior Publication Data

US 2009/0130043 A1 May 21, 2009

(30) Foreign Application Priority Data

May 22, 2006 (WO) ................. PCT/IB2006/051622

(51) Int. Cl.
C07C 39/14 (2006.01)
C07C 69/76 (2006.01)
C11D 3/50 (2006.01)
C11D 9/44 (2006.01)
A61K 8/18 (2006.01)

(52) U.S. Cl. ........................ 568/736; 560/100; 512/19; 510/104

(58) Field of Classification Search ................. 568/736; 560/100
See application file for complete search history.

(56) References Cited

U.S. PATENT DOCUMENTS 4,671,798 A 6/1987 Tarchini ........................ 8/522
5,114,915 A 5/1992 Fehr et al. ..................... 512/15

FOREIGN PATENT DOCUMENTS

EP 167 709 1/1986
EP 465 936 B1 1/1992
EP 1 605 035 B1 12/2005

OTHER PUBLICATIONS

International Search Report PCT/IB2007/051654 Dated Oct. 16, 2007.
Goverdhan Mehta et al., *Terpenes and Related Systems XIII Regiospecific Fragmentation of Patchoulol: A Short Synthesis of α-Bulnesene*, Tetrahedron Letters, vol. 50, 1975, pp. 4495-4498; Pergamon Press (XP-002453448).

*Primary Examiner*—Sikarl A Witherspoon
(74) *Attorney, Agent, or Firm*—Winston & Strawn LLP

(57) ABSTRACT

The present invention relates to the use as perfuming ingredients of certain derivatives of perhydro-1-naphthalenol of formula:

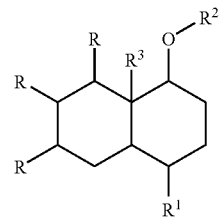

(I)

wherein, in particular, each R represents a hydrogen atom or a methyl group, $R^1$ and $R^3$ represent a methyl or ethyl group, and $R^2$ represents a hydrogen atom or a lower acyl group.

9 Claims, No Drawings

PATCHOULI ODORANT

This application is a 371 filing of International Patent Application PCT/IB2007/05164 filed May 3, 2007.

TECHNICAL FIELD

The present invention relates to the field of perfumery. More particularly, it concerns some derivatives of perhydro-1-naphthalenol as defined further below and their use in perfumery to confer patchouli type odors. The present invention concerns also the compositions or articles containing said compound.

PRIOR ART

To the best of our knowledge, none of the invention's compounds is known.

Some unsaturated alcohols or ketones, having a similar structure, are known in perfumery as being useful ingredients (see EP 1605035, and the discussion further below). However, nowhere in the prior art it is suggested or anticipated that the present saturated alcohols/esters could be used as perfuming ingredients, and in particular to confer their particular fragrance.

DESCRIPTION OF THE INVENTION

We have now surprisingly discovered that a compound of formula

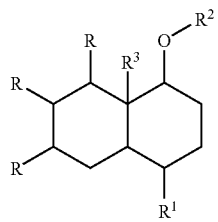

(I)

in the form of any one of its stereoisomers or of a mixture thereof; and wherein each R, simultaneously or independently, represents a hydrogen atom or a methyl group;

$R^1$ represents a methyl or ethyl group;

$R^2$ represents a hydrogen atom or a formyl or acetyl group; and $R^3$ represents a $C_{1-3}$ alkyl group;

can be used as perfuming ingredient, for instance to impart odor of the woody type, having in particular patchouli and/or ambery connotations.

According to a particular aspect of the invention, said compounds of formula (I) are of formula

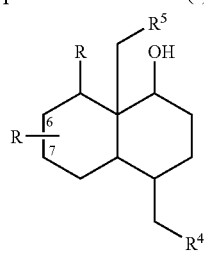

(II)

i.e. with a R group in the position 6 or 7, wherein each R, simultaneously or independently, represents a hydrogen atom or a methyl group;

$R^4$ represents a hydrogen atom or a methyl group; and $R^5$ represents a hydrogen atom or a methyl or ethyl group.

According to another particular aspect of the invention, said compounds of formula (I) are of formula

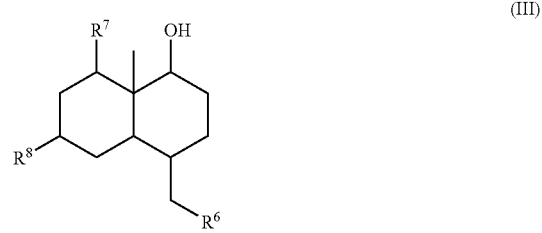

(III)

wherein $R^6$, $R^7$ and $R^8$, simultaneously or independently, represent a hydrogen atom or a methyl group.

In particular in said formula (III), one may cite the ones wherein $R^6$, $R^7$ and $R^8$ are all hydrogen atoms or the ones wherein $R_7$ is a methyl group and one of $R^6$ and $R^8$ is a hydrogen atom and the other a methyl group.

Amongst the invention's compounds, one may cite perhydro-4-ethyl-8,8a-dimethyl-1-naphthalenol, one of the most appreciated by the perfumer. This compound possesses an odor of the woody type with a strong patchouli character. In fact the olfactive note of this compound belongs to the same family, and is close to, as the one of patchouli oil, and could be used as replacer of the known ingredient 2,6,10,10-tetramethyl-1-oxaspirol[4.5]decan-6-ol in a synthetic patchouli. Its overall fragrance can be described as being of the patchouli type with a rooty and ambery aspect.

Others compounds of formula (I) are also described in Table (I) hereinbelow, together with their odors:

TABLE 1

Structure and odor characteristics of the invention's compounds

| Structure of compound (I) | Odor |
|---|---|
| perhydro-4-ethyl-8a-methyl-1-naphthalenol | cedar-patchouli odor with a dried leaves aspect |
| perhydro-4,8a-dimethyl-1-naphthalenol | woody-rooty patchouli and camphoraceous note having a quite natural overall impression |
| perhydro-4,6,8,8a-tetramethyl-1-naphthalenol | patchouli, earthy note quite similar to the one of 2,6,10,10-tetramethyl-1-oxaspirol[4.5]decan-6-ol, but distinguish from the latter by being more woody and a bit less patchouli |
| perhydro-4,6,8a-trimethyl-1-naphthalenol | patchouli, borneol and cellar note |
| perhydro-4,6,8,8a-tetramethyl-1-naphthalenyl acetate | woody-ambery and dry odor which develops its strength over the time |
| perhydro-4,6,8a-trimethyl-1-naphthalenyl formate | woody-ambery and methylionone odor |
| perhydro-4,6,8a-trimethyl-1-naphthalenyl acetate | woody-ambery and with a cedar aspect |

The odor of these compounds distinguishes from the ones of the prior art structural analogues (and in particular the ones disclosed in EP 1605035) by lacking, or by not possessing a significant, citrus-grapefruit notes and/or the cedar, leather, ozone and/or agarwoods notes which are characteristic of the prior art compounds. Said differences lend the invention's compounds and the prior art compounds to be each suitable for different uses, i.e. to impart different organolpetic impressions.

For example perhydro-4-ethyl-8,8a-dimethyl-1-naphthalenol differs from perhydro-4-ethyl-8,8a-dimethyl-1-naphthalenone, the structurally closest analogue disclosed in EP 1605035, by lacking the typical grapefruit note of said prior art compound. Similarly, perhydro-4,6,8,8a-tetramethyl-1-naphthalenol distinguishes itself from the prior art compounds by lacking the citrus-grapefruit.

As mentioned above, the invention concerns the use of a compound of formula (I) as perfuming ingredient, and in particular to confer an odor of the woody-patchouli and/or ambery type. In other words it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing compound (I) and which can be advantageously employed in perfumery industry as active ingredients.

Said compositions, which in fact can be advantageously employed as perfuming ingredient, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono-, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs—und Gehermittel in Lebensmittel, Band 2 der Schriftenreihe Lebensmittelchemie, Lebensmittelqualität, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

Generally speaking, by "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carriers, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords or perfumes possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:
i) as perfuming ingredient, at least one compound of formula (I), as defined above, or an invention's perfuming composition; and
ii) a consumer product base;

is also an object of the present invention.

For the sake of clarity, it has to be mentioned that, by "consumer product base" we mean here a consumer product which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 15% by weight, or even more, of the compounds of the invention based on the weight of the composition into which they are incorporated. Concentrations lower than these, such as in the order of 0.01% to 10% by weight, can be used when these compounds are incorporated into perfumed articles, percentage being relative to the weight of the article.

The invention's compounds can be prepared by hydrogenation/reduction of the corresponding unsaturated alcohol, or the corresponding ketone, described in EP 1605035. A typical example of such manner to prepare the invention's compounds is exposed hereinbelow.

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacements δ are indicated in ppm with respect to TMS as standard, the coupling constants J are expressed in Hz. The NMR spectra are for the mixtures of isomers, unless specified.

EXAMPLE 1

Synthesis of Compounds of Formula (I) by Using the Aldol Derivative of α-Damascone as Starting Material General Procedures:

I) General Procedure for the Diels-Alder Coupling

In a 500 ml reactor were introduced the $AlEtCl_2$, or the $AlCl_3$, 0.1 g of BHT and toluene, or $CH_2Cl_2$. Then, under vigorous stirring, was added the appropriate cyclohexenone dropwise, so as to maintain the temperature below 30° C. Afterwards was added the diene dropwise and when the reaction ended the reaction mixture was hydrolyzed with 5% aqueous HCl, extracted twice with $Et_2O$. The organic layer was then washed with a saturated $NaHCO_3$ aqueous solution, water, brine and then dried over $Na_2SO_4$. Evaporation of the solvents, chromatography ($SiO_2$, elution heptane/AcOEt 98:2) and distillation provided the end product.

II) General Procedure for the Reduction of the Ketone into the Alcohol

In a 100 ml flask, maintained under Ar atmosphere, were introduced 2 molar equivalents, with respect of the ketone, of $LiAlH_4$ in $Et_2O$. Then the appropriate naphthalenone was added dropwise, so as to maintain the reflux. After completion of the reaction the mixture was stirred for 30 minutes at reflux. Afterwards the reaction mixture was hydrolyzed with a stoechiometric amount of aqueous NaOH and the organic layer was dried over $Na_2SO_4$. Evaporation of the solvents and distillation provided the end product.

III) General Procedure for the Hydrogenation of the Naphthalenone into the Perhydro Naphthalenone In a 100 ml flask were introduced the appropriate naphthalenone, ethyl acetate and 10% w/w, relative to the naphthalenone, of $Pd/C_5$%. The mixture was thus stirred under $H_2$, at a room temperature, until consumption of the theoretical amount of hydrogen. Afterwards, the reaction mixture was filtered over Nylon 6/6. Evaporation of the solvents and distillation provided the end product.

IV) General Procedure for the Esterification of the Alcohol

In a 250 ml flask were introduced the appropriate alcohol, $CH_2Cl_2$, dimethylaminopyridine, pyridine and the appropriate carboxylic anhydride. The mixture was thus stirred 24 hours at room temperature. When the reaction has finished the reaction mixture was hydrolyzed with 5% aqueous HCl, extracted twice with $Et_2O$. The organic layer was then washed an aqueous solution of $CuSO_4$, a saturated $NaHCO_3$ aqueous solution, water, brine and then dried over $Na_2SO_4$. Evaporation of the solvents provided the end product.

Perhydro-4,6,8a-trimethyl-1-naphthalenol

Step 1: 4,6,8a-Trimethyl-3,4,4a,5,8,8a-hexahydro-1(2H)-naphthalenone

Prepared according to the general procedure # I, with the following quantities 2,4-Dimethyl-2-cyclohexen-1-one (40 g, 0.32 mmol), Aluminium trichloride (10.7 g, 0.08 mmol), Isoprene (326 g, 4.8 mol), Toluene (500 ml)

The compound was obtained as a mixture of isomers (87/4/9) in 83% yield.

B.p.=78° C./0.003 mbar $^{13}C$-NMR (major isomer): 215.68; 130.73; 117.13; 47.83; 46.86; 37.29; 35.02; 32.14; 29.76; 28.82; 23.84; 20.15; 20.04.

¹H-NMR (major isomer): 0.93 (d, J=7 Hz, 3H); 1.07 (s, 3H); 1.27-1.43 (m, 2H); 1.60-1.86 (m, 2H); 1.68 (broad s, 3H); 1.92-2.15 (m, 3H); 2.22-2.45 (m, 2H); 2.70-2.80 (m, 1H); 5.32 (broad s, 1H).

Step 2: Perhydro-4,6,8a-trimethyl-1-naphthalenone

Prepared according to the general procedure # III, with the following quantities:
Naphthalenone obtained in step 1 (10 g; 0.052 mol), 5% Pd—C (1 g), EtOAc (200 ml), H$_2$ (1.16 l)
The product was obtained in 98% yield as a mixture of isomers (4/16/80).
B.p.=85° C./0.017 mbar
¹H-NMR: 0.81-0.98 (m, 6H); 1.12-1.78 (m, 11H); 1.85-2.30 (m, 4H); 2.52-2.72 (m, 1H).

Step 3: Perhydro-4,6,8a-trimethyl-1-naphthalenol

Prepared according to the general procedure # II, with the following quantities:
Naphthalenone obtained in step 2 (4.0 g; 0.0206 mol), Lithium aluminium hydride (0.39 g; 0.0103 mol), Ether (40 ml)
The title compound was obtained in 91% yield as a mixture of isomers (8/67/6/15).
B.p.=79° C./0.004 mbar
1H-NMR: 0.80-0.92 (m; 7H); 0.94-1.15 (m, 6H); 1.20-2.05 (m, 10H); 3.22-3.56 (m, 1H).

Perhydro-4,6,8a-trimethyl-1-naphthalenyl acetate

The title compound was obtained according to the general procedure IV, with the following quantities:
Perhydro-4,6,8a-trimethyl-1-naphthalenol ((1.8 g, 0.0094 mol), Acetic anhydride (1.43 g, 0.014 mol), Pyridine (1.26 g, 0.016 mol), Dimethylaminopyridine (0.11 g, 0.54 mmol), Dichloromethane (20 ml).
The title compound was obtained in 72% yield as a mixture of isomers (10/70/15).
B.p.=72° C./0.004 mbar
¹H-NMR: 0.80-1.18 (m, 12H); 1.20-1.90 (m, 10H); 2.00-2.07 (m, 3H); 4.57 (m, 1H)

Perhydro-4,6,8a-trimethyl-1-naphthalenyl formate

Prepared according to the general procedure IV, with the following quantities:
Perhydro-4,6,8a-trimethyl-1-naphthalenol (2.0 g, 0.01 mol), Acetic anhydride (3.06 g, 0.03 mol) and formic acid (1.66 g, 0.036 mol) heated together at 55° C. for 2 hours, Dichloromethane (20 ml)
The title compound was obtained in 93% yield as a mixture of isomers (15/56/8/3/18).
B.p.=64° C./0.002 mbar
¹H-NMR: 0.80-1.20 (m, 11H); 1.23-2.10 (m, 11H); 4.65-4.72 (m, 1H); 8.09 (m, 1H).

Perhydro-4,6,8,8a-tetramethyl-1-naphthalenol

Step 1: 4,6,8,8a-Tetramethyl-3,4,44,5,8,8a-hexahydro-1(2H)-naphthalenone

Prepared according to the general procedure # I, with the following quantities:
2,4-Dimethyl-2-cyclohexen-1-one (7.25 g, 0.0585 mol), Ethyl aluminium dichloride (1 molar solution in hexane, 29.2 ml, 0.0292 mol), Methylpentadiene (70% chemical purity, 16.7 g, 0.117 mol), Dichloromethane (150 ml)
The compound was obtained in 90% yield as a mixture of isomers (89/11).
B.p.=85° C./0.065 mbar
¹H-NMR: 0.72-1.02 (m, 6H); 1.15-1.47 (m, 4H); 1.58-2.78 (m, 11H); 5.08-5.38 (m, 1H).

Step 2: perhydro-4,6,8,8a-tetramethyl-1-naphthalenone

Prepared according to general procedure # III, with the following quantities:
Unsaturated ketone obtained in step 1 (4.5 g; 0.022 mol), 5% Pd-C (0.45 g), EtOAc (40 ml), H$_2$ (0.55 l)
The compound was obtained in 95% yield as a mixture of isomers (2/3/63/18/7/3/2/3).
B.p.=74° C./0.008 mbar
1H-NMR: 0.60-1.10 (m, 7H); 1.10-1.80 (m; 13H); 1.90-2.70 (m, 4H).

Step 3: perhydro-4,6,8,8a-tetramethyl-1-naphthalenol

Prepared according to the general procedure # III, with the following quantities:
Ketone obtained in step 2 (3.05 g, 0.0147 mol), Lithium aluminium hydride (0.28 g, 0.0073 mol), Diethylether (20 ml)
The title compound was obtained in 92% yield as a mixture of isomers (4/2/77/10/2/3).
B.p.=74° C./0.034 mbar
¹H-NMR: 0.78-1.10 (m, 10H); 1.12-1.50 (m, 9H); 1.50-2.12 (m, 6H); 3.30-3.80 (m, 1H).

Perhydro-4,6,8,8a-tetramethyl-1-naphthalenyl acetate

Prepared according to the general procedure # IV, with the following quantities:
Perhydro-4,6,8,8a-tetramethyl-1-naphthalenol (0.90 g, 0.0043 mol), Acetic anhydride (0.66 g, 0.0064 mol), Pyridine (0.58 g, 0.0073 mol), Dimethylaminopyridine (0.052 g, 0.43 mmol), Dichloromethane (20 ml)
The title compound was obtained in 76% yield as a mixture of isomers (2/4/53/30/6).
B.p.=78° C./0.034 mbar
¹H-NMR: 0.80-0.98 (m, 9H); 1.90-1.95 (m, 16H); 2.00-2.20 (m, 3H).

Perhydro-4,8a-dimethyl-1-naphthalenol

Step 1: 4,8a-Dimethyl-3,4,4a,5,8,8a-hexahydro-1(2H)-naphthalenone

Prepared according the general procedure # I, with the following quantities:
2,4-Dimethyl-2-cyclohexen-1-one (10.0 g, 0.081 mol), Butadiene (8.75 g, 0.162 mol), Ethyl aluminium dichloride (1 molar solution in hexane, 40 ml, 0.040 mol), Dichloromethane (100 ml)
The compound was obtained in 43% yield as a mixture of isomers (55/45).

B.p=85° C./1.1 mbar

1H-NMR: 0.95 (m, 3H); 1.12-1.45 (m, 4H); 1.60-2.45 (m, 7H); 2.60-2.80 (m, 2H); 5.55-5.68 (m, 2H).

Step 2: perhydro-4,8a-dimethyl-1-naphthalenone

Prepared according to the general procedure # III, with the following quantities:

Unsaturated ketone obtained in step 1 (3.0 g, 0.017 mol), 5% Pd—C (0.3 g), EtOAc (30 ml), $H_2$ (0.38 l)

The compound was obtained in 89% yield as a mixture of isomers (44.4/55.6).

B.p.=85° C./0.017 mbar $^1$H-NMR: 0.80-0.98 (m, 4H); 1.10-2.00 (m, 12H); 2.07-2.30 (m, 2H); 2.45-2.70 (m, 2H).

Step 3: Perhydro-4,8a-dimethyl-1-naphthalenol

Prepared according to general procedure # II, with the following quantities:

Ketone obtained in step 2 (2.0 g, 0.011 mol), Lithium aluminium hydride (0.21 g, 0.0055 mol), Diethyl ether (20 ml)

The title compound was obtained in 83% yield as a mixture of isomers (23/50/26).

B.p.=93° C./0.97 mbar $^1$H-NMR: 0.78-1.12 (m, 8H); 1.14-2.08 (m, 13H); 3.22-4.02 (m, 1H).

Perhydro-4-ethyl-8a-methyl-1-naphthalenol

Step 1: 4-Ethyl-8a-methyl-3,4,4a,5,8,8a-hexahydro-1(2H)-naphthalenone

Prepared according to the general procedure # I, with the following quantities: 4-Ethyl-2-methyl-2-cyclohexen-1-one (27.6 g, 0.20 mol), Butadiene (21.6 g, 0.040 mol), Ethyl aluminium dichloride (1 molar solution in hexane, 100 ml, 0.10 mol), Dichloromethane (300 ml)

The compound was obtained in 42% yield as a mixture of isomers (61/39).

B.p.=76° C./0.021 mbar $^1$H-NMR: 0.82-0.98 (m, 3H); 1.10-1.45 (m, 5H); 1.55-1.80 (m, 3H); 1.90-2.46 (m, 5H); 2.62-2.77 (m, 2H); 5.52-5.68 (m, 2H).

Step 2: Perhydro-4-ethyl-8a-methyl-1-naphthalenone

Prepared according to the general procedure # III, using the following quantities:

Unsaturated ketone obtained in step 1 (5.0 g, 0.026 mol), 5% Pd—C (0.5 g), EtOAc (50 ml)

$H_2$ (0.6 l)

The compound was obtained in 97% yield as a mixture of isomers (40/60).

B.p.=84° C./0.048 mbar $^1$H-NMR: 0.82-0.95 (m, 3H); 1.08-1.75 (m, 14H); 1.80-2.36 (m, 4H); 2.52-2.63 (m, 1H).

Step 3: Perhydro-4-ethyl-8a-methyl-1-naphthalenol

Prepared according to the general procedure # II, with the following quantities:

Ketone obtained in step 2 (3.40 g, 0.0175 mol), Lithium aluminium hydride (0.33 g, 0.00875 mol), Diethyl ether (30 ml)

The title compound was obtained in 99% yield as a mixture of isomers (11/21/4/64).

B.p.=86° C./0.055 mbar

1H-NMR: 0.78-1.10 (m, 6H); 1.12-1.96 (m, 17H); 3.22-4.03 (m, 1H).

Perhydro-4-ethyl-8,8a-dimethyl-1-naphthalenol

Step 1: 4-Ethyl-8,8a-dimethyl-3,4,4a,5,8,8a-hexahydro-1(2H)-naphthalenone

Prepared according to the general procedure I, with the following quantities:

4-Ethyl-2-methyl-2-cyclohexen-1-one (20.7 g, 0.15 mol), Piperylene (50% chemical purity, 40.8 g, 0.30 mol), Ethyl aluminium dichloride (1 molar solution in hexane, 30 ml, 0.03 mol), Dichloromethane (200 ml)

The title compound was obtained in 72% yield as a mixture of isomers (63/37).

B.p.=81° C./0.034 mbar $^1$H-NMR: 0.76-1.30 (m, 9H); 1.42-1.83 (m, 4H); 1.90-2.37 (m, 6H); 2.50-2.77 (m, 1H); 5.37-5.62 (m, 2H).

Step 2: perhydro-4-ethyl-8,8a-dimethyl-1-naphthalenone

Prepared according to the general procedure # III, with the following quantities:

Unsaturated ketone obtained in step 1 (5.0 g, 0.025 mol), 5% Pd—C (0.5 g), EtOAc (50 ml), $H_2$ (0.625 l).

The title compound was obtained in 98% yield as a mixture of isomers (42/38/18).

B.p.=86° C./0.036 mbar $^1$H-NMR: 0.60-1.20 (m, 7H); 1.20-1.90 (m, 13H); 1.95-2.40 (m, 3H); 2.50-2.70 (m, 1H).

Step 3: Perhydro-4-ethyl-8,8a-dimethyl-1-naphthalenol

Prepared according to the general procedure # II, with the following quantities:

Starting ketone obtained in step 2 (3.90 g, 0.018 mol), Lithium aluminium hydride (0.34 g, 0.009 mol), Diethyl ether (30 ml)

The title compound was obtained in 99% yield as a mixture of isomers (33/7/40/17)

B.p.=90° C./0.032 mbar $^1$H-NMR: 0.78-1.17 (m, 10H); 1.20-2.12 (m, 15H); 3.22-3.82 (m, 1H).

EXAMPLE 2

Preparation of a Perfuming Composition

A perfuming base was prepared by admixing the following ingredients:

| Ingredient | Parts by weight |
| --- | --- |
| Styrallyl acetate | 10 |
| Allyl amyl glycolate | 5 |
| 10%* 4-Nonanolide | 5 |
| Bergamote essential oil | 100 |

-continued

| Ingredient | Parts by weight |
| --- | --- |
| Coumarine | 15 |
| 10%* Damascone delta | 5 |
| 3,7-Dimethyl-1,6-nonadien-3-ol | 50 |
| 10%* 2-Ethyl-3-hydroxy-4(4H)-pyranone | 20 |
| Florol ®[1)] | 100 |
| 3-(4-Methoxyphenyl)-2-methylpropanal | 30 |
| Lilyflore ®[2)] | 20 |
| Mandarine essential oil | 10 |
| Nutmeg | 10 |
| Hedione ®[3)] | 300 |
| 1,2,3,4,4aβ,5,8,8aβ-Octahydro-2,2,6, 8α-tetramethyl-1α-naphthalenol | 5 |
| Portugal Bresil essential oil | 20 |
| Romandolide ®[4)] | 150 |
| Pipol salicylate | 20 |
| Vanilline | 15 |
| 10%* 2,4-Dimethyl-3-cyclohexene-1-carbaldehyde | 30 |
|  | 920 |

*in dipropyleneglycol

[1)]Tetrahydro-2-isobutyl-4-methyl-4(2H)-pyranol; origin: Firmenich S A, Geneva, C H

[2)]2,5-Dimethyl-2-indanmethanol; origin: Firmenich S A, Geneva, C H

[3)]Methyl dihydrojasmonate; origin: Firmenich S A, Geneva, C H

[4)](1S,1'R)-[1-(3',3'-Dimethyl-1'-cyclohexyl)ethoxycarbonyl]methyl propanoate; origin: Firmenich S A, Geneva, C H The addition of 80 parts by weight of perhydro-4-ethyl-8, 8a-dimethyl-1-naphthalenol to the above-described perfuming composition imparted to the latter an excellent woody character very close to the one of patchouli. Furthermore a camphoraceous aspect is developed, which impart to the new fragrance a nice freshness in the head-notes. Upon evaporation of the perfuming composition, the ambery aspect of the invention's compounds became more perceivable, adding thus a new pleasant effect to the patchouli dimension.

When to the above-mentioned perfuming base was added the same amount of patchouli the new fragrance was earthier and less elegant than the one obtained with the invention's compound.

When to the above-mentioned perfuming base was added the same amount of 4-ethyl-6,8-dimethyl-1,2,3,4,4a,5,8,8a-octahydro-1-naphthalenol (a perfuming ingredient from the prior art) the base scent acquired a different woody character, which was of the vetiver type, furthermore it acquired also a grapefruit character which modified strongly the whole fragrance (less oriental type)

When to the above-mentioned perfuming base was added the same amount of perhydro-4-ethyl-8-methyl-1-naphthalenone (a perfuming ingredient from the prior art) the base scent acquired a powerful sweet-powdery woody note with a vetyver type connotation. When to the above-mentioned perfuming base was added the same amount of perhydro-4-ethyl-8,8a-dimethyl-1-naphthalenone (a perfuming ingredient from the prior art) the base scent acquired a vetyver and grapefruit character, no patchouli note was perceivable.

The invention claimed is:

1. A compound of formula

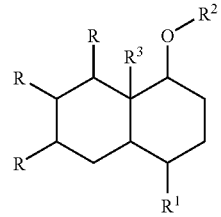

(I)

in the form of any one of its stereoisomers or of a mixture thereof; and wherein:
each R, simultaneously or independently, represents a hydrogen atom or a methyl group;
$R^1$ represents a methyl or ethyl group;
$R^2$ represents a hydrogen atom or a formyl or acetyl group; and
$R^3$ represents a $C_{1-3}$ alkyl group.

2. The compound according to claim 1, having the formula:

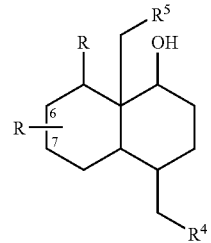

(II)

wherein:
each R, simultaneously or independently, represents a hydrogen atom or a methyl group;
$R^4$ represents a hydrogen atom or a methyl group; and
$R^5$ represents a hydrogen atom or a methyl or ethyl group.

3. The compound according to claim 2, having the formula:

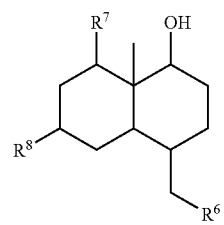

(III)

wherein $R^6$, $R^7$ and $R^8$, simultaneously or independently, represents a hydrogen atom or a methyl group.

4. The compound according to claim 1, specifically as perhydro-4-ethyl-8,8a-dimethyl-1-naphthalenol, perhydro-4-ethyl-8a-methyl-1-naphthalenol, perhydro-4,8a-dimethyl-1-naphthalenol, perhydro-4,6,8,8a-tetramethyl-1-naphthalenol, perhydro-4β,6β,8aβ-trimethyl-4aβH-1α-naphthalenol, perhydro-4,6,8,8a-tetramethyl-1-naphthalenyl acetate, perhydro-4β,6β,8aβ-trimethyl-4aαH-1α-naphthalenyl formate or perhydro-4,6,8a-trimethyl-1-naphthalenyl acetate.

5. The compound according to claim 1, specifically as perhydro-4-ethyl-8,8a-dimethyl-1-naphthalenol, perhydro- 4-ethyl-8a-methyl-1-naphthalenol, perhydro-4,8a-dimethyl-1-naphthalenol, perhydro-4,6,8,8a-tetramethyl-1-naphthalenol, or perhydro-4β,6β,8aβ-trimethyl-4aβH-1α-naphthalenol.

6. A perfuming ingredient in the form of a composition comprising:
at least one compound of formula:

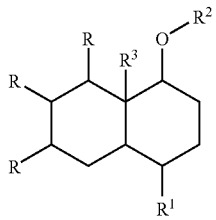
(I)

in the form of any one of its stereoisomers or of a mixture thereof; and wherein:
each R, simultaneously or independently, represents a hydrogen atom or a methyl group;
$R^1$ represents a methyl or ethyl group;
$R^2$ represents a hydrogen atom or a formyl or acetyl group; and
$R^3$ represents a $C_{1-3}$ alkyl group; and
at least one ingredient selected from the group consisting of a perfumery carrier and a perfumery base;
and optionally at least one perfumery adjuvant.

7. A perfumed article comprising:
as perfuming ingredient, at least one compound of formula:

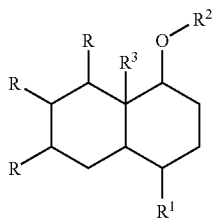
(I)

in the form of any one of its stereoisomers or of a mixture thereof; and wherein:
each R, simultaneously or independently, represents a hydrogen atom or a methyl group;
$R^1$ represents a methyl or ethyl group;
$R^2$ represents a hydrogen atom or a formyl or acetyl group; and
$R^3$ represents a $C_{1-3}$ alkyl group; and
a consumer product base.

8. The perfumed article according to claim 7, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

9. A method to confer, enhance, improve or modify the odor properties of a perfuming composition or of a perfumed article, which method comprises adding to said composition or article an effective amount of at least a compound of formula:

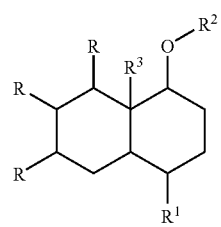
(I)

in the form of any one of its stereoisomers or of a mixture thereof; and wherein:
each R, simultaneously or independently, represents a hydrogen atom or a methyl group;
$R^1$ represents a methyl or ethyl group;
$R^2$ represents a hydrogen atom or a formyl or acetyl group; and
$R^3$ represents a $C_{1-3}$ alkyl group.

* * * * *